United States Patent
Barlet (10) Patent No.: US 10,575,932 B1
(45) Date of Patent: Mar. 3, 2020

(54) ORAL CARE APPLIANCE AND METHOD OF OPERATING THEREOF

(71) Applicant: Willo 32 SAS, Limoges (FR)

(72) Inventor: David Aurélien Barlet, Rilhac-Rancon (FR)

(73) Assignee: Willo 32 SAS, Limoges (FR)

(*) Notice: Subject to any disclaimer, the term of this patent is extended or adjusted under 35 U.S.C. 154(b) by 0 days.

(21) Appl. No.: 16/269,954

(22) Filed: Feb. 7, 2019

(51) Int. Cl.
*A61C 17/22* (2006.01)
*A61C 17/02* (2006.01)

(52) U.S. Cl.
CPC ........ *A61C 17/221* (2013.01); *A61C 17/0211* (2013.01); *A61C 17/0217* (2013.01); *A61C 17/228* (2013.01)

(58) Field of Classification Search
CPC ....... A61C 17/16; A61C 17/22; A61C 17/221; A61C 17/222; A61C 17/225; A61C 17/227; A61C 17/30; A61C 17/32; A61C 17/38; A61C 7/227; A61B 15/0012; A61B 2200/1066
See application file for complete search history.

(56) References Cited

U.S. PATENT DOCUMENTS

| | | | | |
|---|---|---|---|---|
| 4,223,417 A | * | 9/1980 | Solow | A46B 9/045 15/167.2 |
| 4,346,492 A | * | 8/1982 | Solow | A46B 7/06 15/22.1 |
| 5,327,608 A | * | 7/1994 | Kosakewich | A46B 7/02 15/167.1 |
| 6,893,259 B1 | * | 5/2005 | Reizenson | A61C 17/0211 433/29 |
| 7,082,638 B2 | | 8/2006 | Koh | |
| 7,537,451 B1 | | 5/2009 | Ramnarine | |
| 8,341,790 B2 | * | 1/2013 | Van Baren | A61C 17/222 15/22.1 |
| 8,359,692 B2 | * | 1/2013 | Brewer | A46B 9/045 15/167.2 |
| 8,448,282 B2 | | 5/2013 | Stapelbroek | |
| 8,578,539 B2 | * | 11/2013 | Jousma | A61C 17/222 15/167.1 |
| 8,617,090 B2 | | 12/2013 | Fougere | |
| 8,635,731 B2 | | 1/2014 | Garner | |
| 8,667,634 B2 | | 3/2014 | Steur | |
| 8,677,541 B2 | * | 3/2014 | Meadows | A61C 17/0211 15/22.1 |
| 8,745,802 B2 | | 6/2014 | Steur | |

(Continued)

FOREIGN PATENT DOCUMENTS

| | | |
|---|---|---|
| EP | 2654609 B1 | 3/2018 |
| EP | 2654611 B1 | 4/2018 |

(Continued)

*Primary Examiner* — Ralph A Lewis
(74) *Attorney, Agent, or Firm* — Daylight Law, P.C.

(57) ABSTRACT

This disclosure relates to an oral care appliance and a method for use in oral care for cleaning the teeth of one or two arches using a mouthpiece forming a closed or nearly closed cavity. The mouthpiece is adapted to deform in response to pressure variations inside the cavity and create an action on the teeth. This disclosure includes a description of depression chambers and associated methods that can contribute to the operation of the oral care appliance by affecting the aforementioned pressure variations.

35 Claims, 8 Drawing Sheets

(56) References Cited

U.S. PATENT DOCUMENTS

| | | | |
|---|---|---|---|
| 8,863,346 | B2 | 10/2014 | Headstrom |
| 8,978,189 | B1 | 3/2015 | Sexton |
| 8,990,992 | B2 | 3/2015 | Stapelbroek |
| 9,084,655 | B2 | 7/2015 | Sahoo |
| 9,277,980 | B2 | 3/2016 | Leveling |
| 9,308,065 | B2 | 4/2016 | Steiner |
| 9,504,542 | B2 * | 11/2016 | De Gentile ........ A61C 17/0211 |
| 9,526,597 | B2 | 12/2016 | Steur |
| 9,636,195 | B2 | 5/2017 | Wolpo |
| 9,636,197 | B2 | 5/2017 | Khangura |
| 9,668,840 | B2 | 6/2017 | Miller |
| 9,907,633 | B2 | 3/2018 | Wolpo |
| 2007/0184404 | A1 | 8/2007 | Johnki |
| 2016/0113745 | A1 | 4/2016 | Golub |
| 2016/0135581 | A1 | 5/2016 | Pai |
| 2016/0206415 | A1 | 7/2016 | Kraft |
| 2016/0270892 | A1 | 9/2016 | Yoo |
| 2017/0367801 | A1 | 12/2017 | Fitzgerald |
| 2018/0000573 | A1 | 1/2018 | Miller |
| 2018/0184795 | A1 | 7/2018 | Pai |
| 2018/0184857 | A1 | 7/2018 | Pai |

FOREIGN PATENT DOCUMENTS

| | | |
|---|---|---|
| WO | 2017061980 A1 | 4/2017 |
| WO | 2017146366 A1 | 8/2017 |
| WO | 2018160986 A1 | 9/2018 |

* cited by examiner

FIG. 12

ORAL CARE APPLIANCE AND METHOD OF OPERATING THEREOF

BACKGROUND OF THE INVENTION

Dental cleaning plays a significant role in impacting the overall health of an individual. Many people schedule regular visits to a dentist for regular check-up's and cleaning operations. Many devices have been developed over the years to achieve the purpose of oral hygiene. These devices are either electrical or non-electrical. Among the above-mentioned categories of dental cleaning devices, electric dental units have gained popularity. Some examples of electric dental units are electric toothbrushes, dental water jets and electric flosses which intend to provide cleaning results by eradicating the food remains, plaque, etc from the spaces in between the teeth. These devices tend to require less user intervention in their operation and some are also suitable for people with reduced mobility or people on the move for whom it is difficult to use a traditional toothbrush. However, it is necessary to provide and improve existing dental units for ensuring satisfactory cleaning results.

One drawback of existing oral care appliances is the limited efficiency and durability of their electrical components which reduces the appliance's useful life. The components of the dental cleaning units may suffer degradation during the drainage and release operation of the waste material from the user's mouth. For example, the electrical components can be exposed to foam or waste which may affect their operation as well as decrease the lifetime of these components. There may also be some moving parts in the dental units which require maintenance. As such, the overall maintenance cost of the electrical dental units can be increased due to degradation of these components.

SUMMARY OF THE INVENTION

Specific embodiments of the present invention disclosed herein relate to the technical field of oral care appliances and methods of use thereof. In particular, specific embodiments of the present invention disclosed herein relate to oral care appliances for dental cleaning.

Specific embodiments of the present invention disclosed herein overcome one or more of the above-mentioned problems with an oral care appliance and a method for operating such appliance. These solutions provide an easy to maintain and convenient oral care appliance. They furthermore reduce the time required to dedicate to oral hygiene. The oral care appliance may be used for cleaning, whitening and in other general oral care applications.

An oral care application in accordance with specific embodiments of the present invention includes a mouthpiece comprising a flexible membrane configured to deform in response to pressure variations generated in a cavity resulting in volume changes of the cavity, and a depression chamber having a plurality of apertures and means for generating pressure variations in the cavity. A first aperture of the depression chamber is engaged with a first pump operatively generating a vacuum in the depression chamber and a second aperture of the depression chamber is connected to the mouthpiece through a connecting line.

A method of operating an oral care appliance in a brushing cycle in accordance with specific embodiments of the present invention includes generating a vacuum in a depression chamber by means of a first pump attached to a first aperture of the depression chamber, opening a first valve coupled to a connecting line between a mouthpiece and a second aperture of the depression chamber to create a pressure difference in the mouthpiece to facilitate the contraction of the mouthpiece on a dental arch of a user and thereby aspirating a fluid out the mouthpiece to the depression chamber through the connecting line, and closing the first valve to facilitate the relaxation of the mouthpiece wherein vacuum is again created in the depression chamber by means of the first pump.

DETAILED DESCRIPTION OF THE PREFERRED EMBODIMENT

Aspects of the present invention can be understood by reference to the figures and description set forth herein. However, the following descriptions, and numerous specific details thereof, are given by way of illustration and not of limitation. Many changes and modifications to the specific descriptions may be made without departing from the spirit and scope thereof, and the present invention includes all such modifications. It is to be understood that the embodiments may or may not overlap with each other. Thus, part of one embodiment, or specific embodiments thereof, may or may not fall within the ambit of another, or specific embodiments thereof, and vice versa.

Aspects of specific embodiments of the present invention will be presented by describing various embodiments using specific examples and represented in different figures. For clarity and ease of description, each aspect includes only a few embodiments. Different embodiments from different aspects may be combined or practiced separately, to design a customized process depending upon application requirements. Many different combinations and sub-combinations of a few representative processes shown within the broad framework of this invention, that may be apparent to those skilled in the art but not explicitly shown or described, should not be construed as precluded.

This disclosure is generally drawn, inter alia, to appliances, systems, and methods to maintain oral care health and hygiene.

Figure 1:
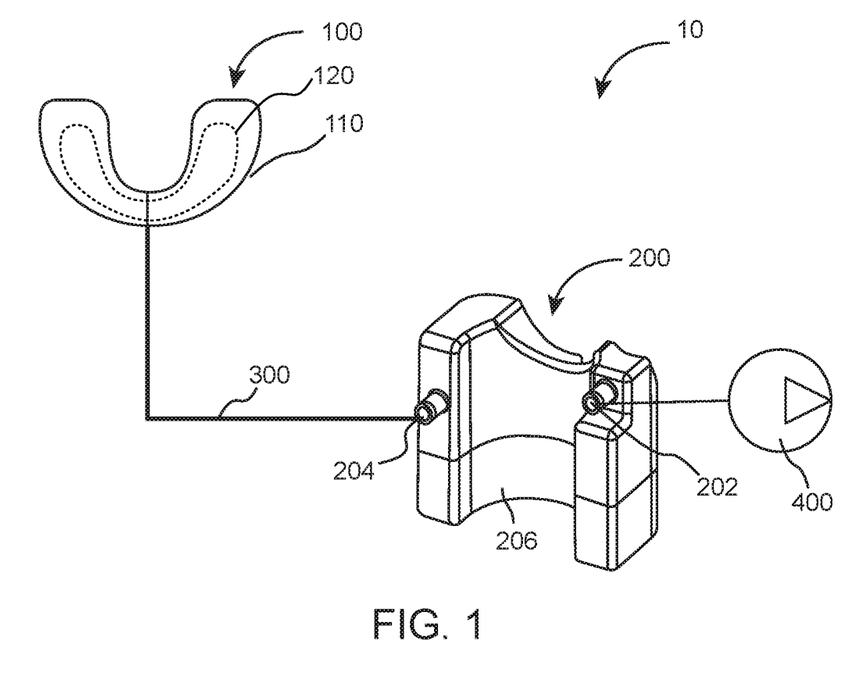
FIG. 1 illustrates an oral care appliance 10 in accordance with specific embodiments of the present invention.

FIG. 1 illustrates an oral care appliance 10 according to the presently disclosed subject matter that comprises a mouthpiece 100 including a flexible membrane 110 configured to deform in response to pressure variations generated in a cavity 120 resulting in volume changes of the cavity 120. The volume of the cavity can increase or decrease depending on the pressure variations inside the cavity. A positive pressure relative to ambient pressure inside the cavity increases its volume and a negative pressure relative to ambient pressure inside the cavity decreases its volume. The oral care appliance 10 further comprises a depression chamber 200 having a plurality of apertures 202, 204 and means for generating pressure variations inside the cavity. The means for generating pressure variations inside the cavity is a reservoir 206 within depression chamber 200 that is in fluid communication with the cavity and that has a controllable variant pressure. Various approaches for adjusting and maintaining the pressure within that reservoir are disclosed herein. The aperture 202 is engaged with a first pump 400 operatively generating a vacuum inside the reservoir 206 of the depression chamber 200 while the aperture 204 is connected to the mouthpiece 100 through a connecting line 300. The pump 400 transforms electrical energy into mechanical work used to move fluid from or into the reservoir 206 of the depression chamber 200. This fluid movement increases or decreases the pressure inside the reservoir 206 of the depression chamber 200.

Figure 2:
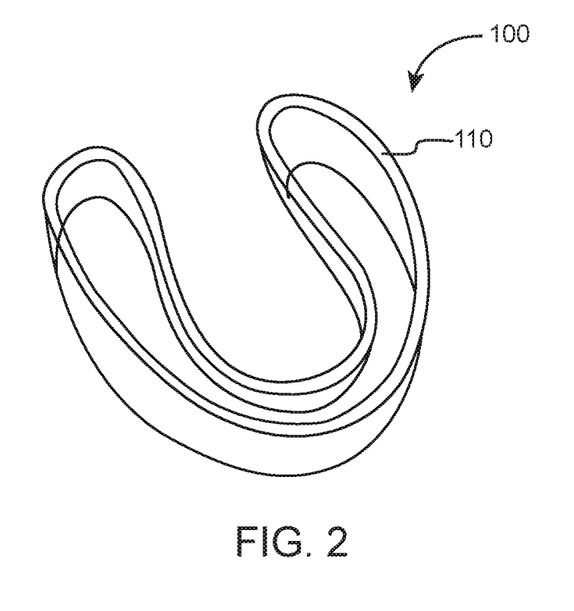
FIG. 2 illustrates a perspective view of a mouthpiece 100 in accordance with specific embodiments of the present invention.

FIG. 2 illustrates the perspective view of the mouthpiece 100 according to an embodiment of the invention. The mouthpiece 100 is preferably made up of flexible/soft material suitable for medical use or oral care. This allows easy insertion inside the mouth of the user providing comfort and reversible deformation. The mouthpiece 100 according to an embodiment of the invention is made up of flexible material impermeable to gases (such as air), liquids (water, cleaning liquid, disinfecting liquid) and any solid (waste particles, debris); such as latex, TPE, silicone, or any other flexible polymer compatible with a medical or oral care use. The mouthpiece 100 as illustrated in FIG. 2, is adapted to be placed on a dental arch of the user, comprises a flexible membrane 110 configured to deform in response to pressure variations inside the cavity 120, where the cavity 120 is a space formed between the dental arch and the flexible membrane 110 or between two layers of the mouthpiece. The gripping pressure changes the contraction of the flexible membrane 110 of the mouthpiece 100 placed on the dental arch of the user.

Figure 3:
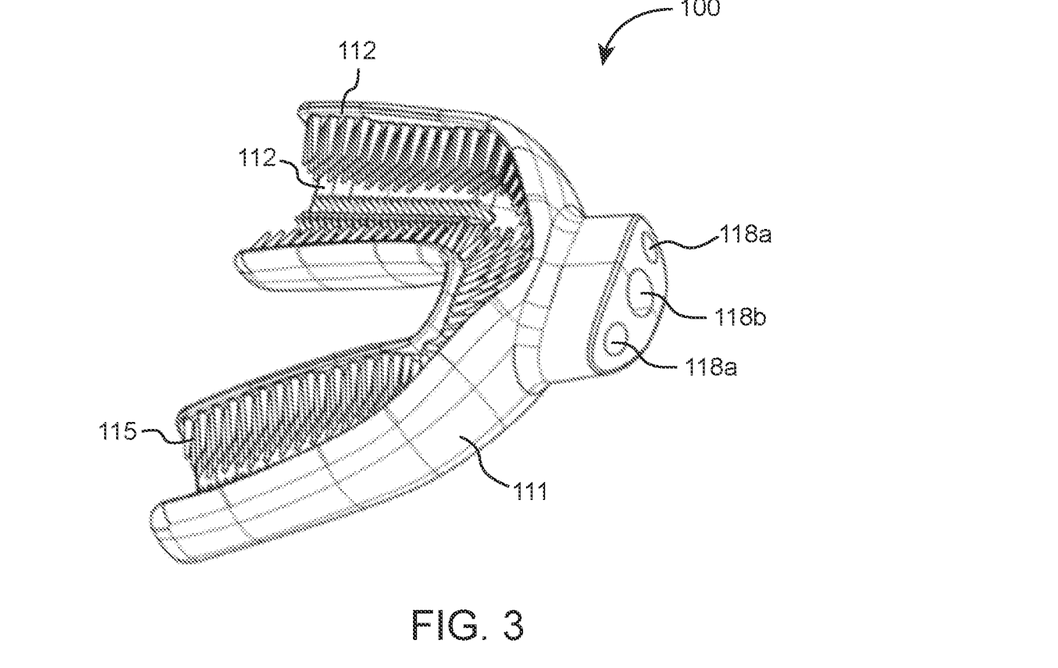
FIG. 3 illustrates a perspective view of the mouthpiece 100 in accordance with specific embodiments of the present invention.

In another embodiment of the invention as shown in FIG. 3, the mouthpiece 100 comprises an outer membrane 111 and an inner membrane 112. The outer membrane 111 and the inner membrane 112 can be made up of similar or different materials compatible to be used in oral care. The mouthpiece 100 further comprises a plurality of holes 118a, 118b for injecting/draining of a fluid/cleaning agent/air into/from the mouthpiece 100. In particular examples, the at least one-hole 118a can be used for injecting the fluid inside the mouthpiece 100 and at least one-hole 118b for draining the fluid out of the mouthpiece 100. In some further particular examples, the holes 118 can be placed on any position on the outer membrane 111. In a different example, a single hole 118 can be used for injecting/draining the fluid/cleaning agent/air. A plurality of cleaning elements 115 is attached to the inner membrane 112. In another particular example, the mouthpiece 100 comprises numerous injection and aspiration ports on its inner membrane 112 to distribute both the aspiration and the injection of fluid evenly in the mouthpiece 100 and thus on the gums and dentition of the user. The cleaning elements 115 can include a set of cylindrical or conical bristles which may be glued, overmolded or attached to the inner membrane by other different means. In specific examples, the shape of the cleaning elements 115 can be conical, cylindrical, flat, pointed tip, tapered, star-shaped, Zig-Zag etc. The cleaning elements 115 can be arranged in different angular arrangements in the mouthpiece 100 to provide effective cleaning around and in between the dental arch. The cleaning elements 115 can be used for removing plaque, debris, inter-dental particles etc. inside the mouth. The outer membrane 111 is configured for contacting on the gum of the user, providing comfort and good hermeticity to the cavity 120 formed by the mouthpiece 100.

The mechanical action of the cleaning elements 115 can consist of rubbing, sliding, deforming, rotating, vibrating or any other particular movement on the surface of the teeth of the user.

In a particular embodiment, the outer membrane 111 is made of rigid material to drive the deformation of the inner membrane 112 toward the teeth. In another embodiment, the shape of the outer membrane 111 is designed to favour the amplitude and gripping pressure of the deformation of the inner membrane 112 toward particular areas of the dentition to improve their cleaning. This particular feature can be achieved by having discontinuity of the volume the cavity or cavities, the thickness, the material, rigidity or the shape of the outer membrane 111 or any other of its characteristics.

In specific embodiments of the invention, the mouthpiece 100 can be an inflatable mouthpiece configured to deform in response to pressure variations in at least one cavity of the inflatable mouthpiece itself. The at least one cavity in case of the inflatable mouthpiece is formed inside the mouthpiece 100 between the inner membrane 112 and the outer membrane 111. The pressure decrease (relative to ambient pressure) in the at least one cavity of the mouthpiece 100, wherein the mouthpiece 100 is inflatable, may result in a relaxation phase of the mouthpiece 100 and vice-versa.

The mouthpiece 100 can be in a form of denture shape or a U-shaped mouthpiece. The mouthpiece 100 may be made-up of soft material which is moulded/pre-shaped in a curved shape forming an arch, U-shape, c-shape, horseshoe shape, or any other shape allowing easy insertion of the mouthpiece around the dental arch of the user. The components of the mouthpiece 100 can be composed of one or more several materials. Examples of materials may include but are not limited to, rubber, plastic, silicon, latex, polymer, thermoplastic elastomers (TPE) and other soft and flexible material suitable for oral care.

Thermoplastic elastomer (TPE) are suitable as flexible materials for oral care applications. They are copolymers consisting in a physical mix of polymers having plastic and elastomeric properties. Furthermore, they have a suitable temperature range of operation, between −10° C. and 80° C. They can have good food and medical grade properties as well as an absence of significant creep. Furthermore, they have good tearing and tensile strength. This makes TPEs suitable for constituting the flexible material of the mouthpiece 100.

Silicone is another polymer suitable as flexible material for oral care applications. It is a very stable polymer with low chemical reactivity. Furthermore it is stable over a large range of temperature (between −100° C. and 250° C.). It also has excellent creep, tear strength and elongation properties. In addition, it also has good food and medical grade properties making suitable for the flexible material of the mouthpiece 100.

For pleasing of the eyes, the inner and outer surface of the mouthpiece can be coloured or transparent with visual effect or not, textured or not.

In an embodiment of the invention, the shape of the mouthpiece 100 is adapted for usage of distinct users by means of adapting angle of the U-shape to match the shape of jaw of the user. In another embodiment, the shape of the mouthpiece may be adapted for adjustment of the mouthpiece to match the height of gingiva and teeth of the user. The adaptability of the mouthpiece according to different shapes and heights of the users provides satisfactory dental cleaning to different users with different configurations of the dental arch.

Figure 4:
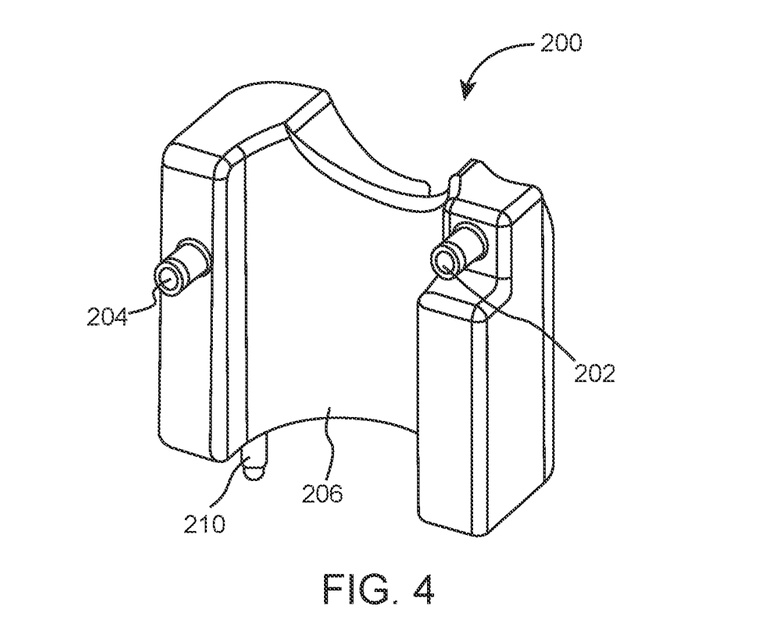
FIG. 4 illustrates a perspective view of a depression chamber 200 in accordance with specific embodiments of the present invention.

FIG. 4 illustrates the depression chamber 200 according to an embodiment of the invention. The depression chamber 200 comprises a plurality of apertures 202, 204 and a reservoir 206 enclosed between the walls of the depression chamber 200. The reservoir 206 acts as means of generating pressure variations in the cavity formed between the mouthpiece 100 and the dental arch of the user. The chamber can be made up of any material selected from a group of plastic, PVC (polyvinyl chloride), ABS (Acrylonitrile Butadiene Styrene), a high-density polyethylene polymer or other such similar materials.

ABS is a thermoplastic copolymer, impact resistant, tough, and with a reasonable heat resistance. ABS is chemically resistant to acids, alkalis and alcohols. ABS is lightweight and injection mouldable. All these properties make it suitable as a material for the depression chamber.

Figure 5:
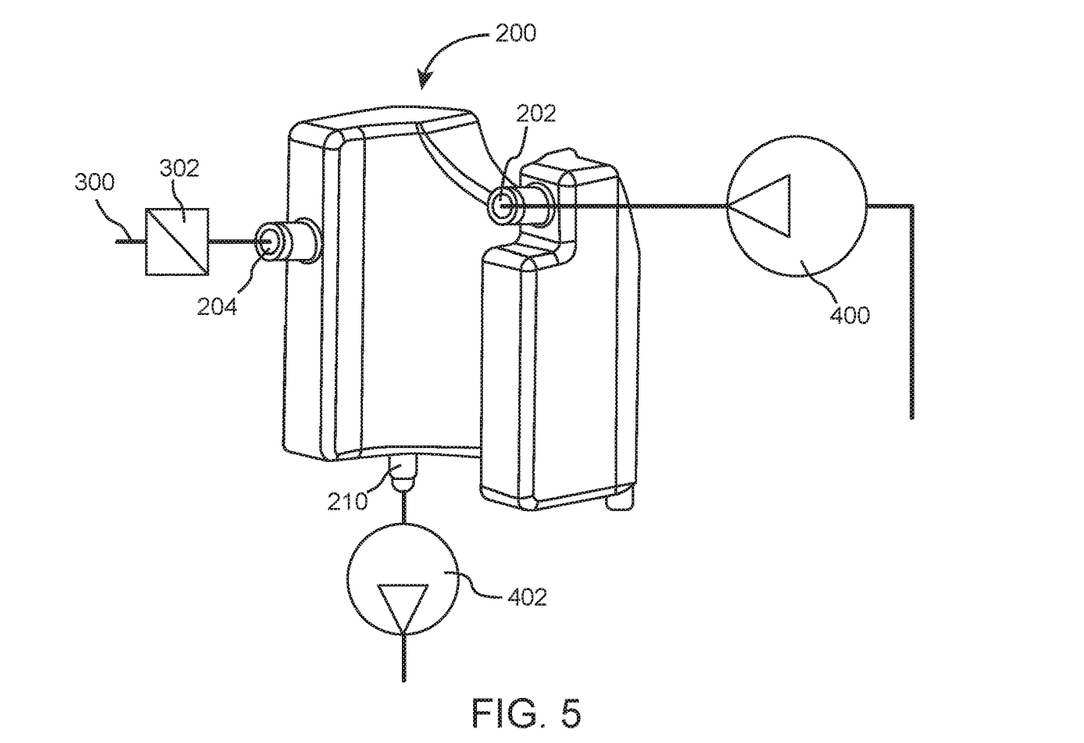
FIG. 5 illustrates the connection of a first pump 400 and a second pump 402 with the depression chamber 200 in accordance with specific embodiments of the present invention.

In still another embodiment of the invention, the first aperture 202 is connected to the first pump 400 as shown in FIG. 5. In some examples, the aperture 202 acts as a vacuum inlet and allows the first pump 400 to create vacuum inside the reservoir 206 by sucking the air out of the reservoir 206. The second aperture 204 of the depression chamber 200 is connected to the mouthpiece 100 through the connecting line 300. In some specific examples, the aperture 204 acts as a waste liquid/fluid inlet passing the waste and the air from the mouthpiece 100 to the depression chamber 200. The air and the waste are aspirated into the depression chamber 200 by the first pump 400. The first pump 400 is operatively engaged to the depression chamber to create the vacuum/depression inside the depression chamber 200; the vacuum thereby creates a pressure difference between the inside of the cavity formed between the mouthpiece 100 and the dental arch and the reservoir 206 of the depression chamber 200; resulting in aspiration of air and waste from the mouthpiece 100 to the depression chamber 200.

In yet another embodiment of the invention, the connecting line 300 comprises a valve mechanism 302 to control the connection between the mouthpiece 100 and the depression chamber 200. In some specific examples, the valve mechanism 302 comprises an electrically or a mechanically operated valve. The valve mechanism 302 is in open position when the air and the waste are aspirated from the mouthpiece 100. According to different examples of the invention, the valve mechanism 302 can be a solenoid valve or a servo-valve, any electronic valve with a pinch valve or a membrane valve. The valve 302 may also be replaced by a valve which is controlled by a pneumatic circuit (i.e. a pneumatic control valve).

In another embodiment of the invention, the depression chamber 200 further comprises a third aperture 210, as shown in FIG. 4 and FIG. 5, which acts as waste outlet to drain the waste from the depression chamber 200. In another specific embodiment of the invention, the third aperture is engaged with a second pump 402 that drains the waste from the depression chamber 200.

According to specific embodiment of the invention, the second pump 402 can be a one-way pump used for draining out waste liquids.

According to another specific embodiment of the invention, the second pump 402 can be a peristaltic pump or any other pump suitable for draining out the waste from the depression chamber 200.

Figure 6A:
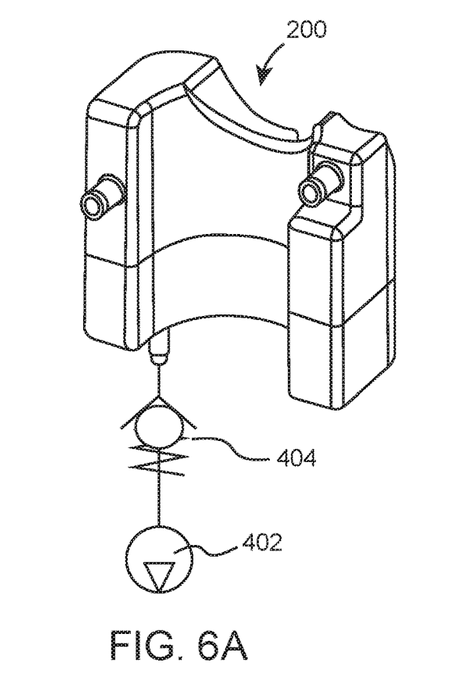
FIG. 6A illustrates a check valve 404 connected between a second pump 402 and the depression chamber 200 in accordance with specific embodiments of the present invention.
Figure 6B:
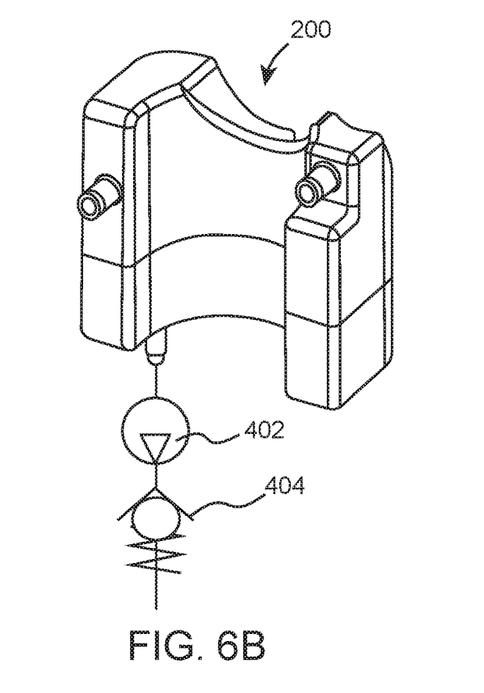
FIG. 6B illustrates the check valve 404 connected between the second pump 402 and a sink in accordance with specific embodiments of the present invention.

According to yet another specific embodiment of the invention as illustrated in FIG. 6A, the second pump 402 can be a two-way pump having a check valve 404 in between the pump 402 and the depression chamber 200. The check valve 404 prevents the air from entering the depression chamber 200 through aperture 210 which would otherwise potentially affect the vacuum created inside the depression chamber 200. According to another embodiment as shown in FIG. 6B, the check valve 404 can also be placed between the pump 402 and a sink.

Figure 6C:
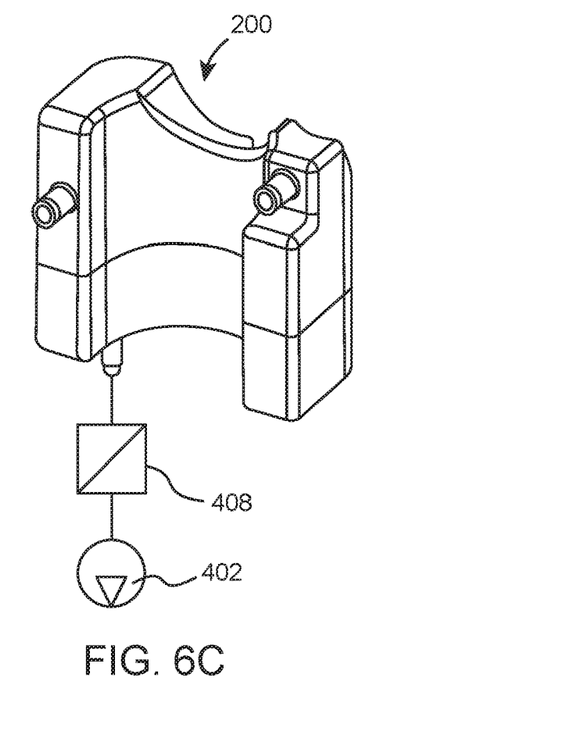
FIG. 6C illustrates an electrically operated valve 408 engaged between the second pump 402 and the depression chamber 200 in accordance with specific embodiments of the present invention.

In still another embodiment of the invention as shown in FIG. 6C, an electrically operated valve 408 is engaged between the second pump 402 and the depression chamber 200. The valve 408 is closed when the vacuum is created in the depression chamber 200. This aids in isolating or cancelling the depression formed in the depression chamber 200. The valve 408 is in open position during the draining of the waste at the end of a cycle or when there is sufficient waste inside the depression chamber 200. After the waste is drained completely from the depression chamber 200, the valve 408 closes.

According to another specific embodiment of the invention, the user may manually drain or empty the depression chamber 200. According to different specific examples, the depression chamber 200 can be removable or detachable from the oral care appliance 10.

In yet another embodiment of the present invention, the depression chamber 200 prevents foam and fluid from flowing through the first pump 400 while the second pump 402 drains the fluid out of the depression chamber 200.

According to different examples of the invention, the pumps 400, 402 may be connected in various arrangements to the depression chamber 200. In a specific example, the first pump 400 may be connected on an upper portion of the depression chamber 200 and the second pump 402 may be connected to a lower portion of the depression chamber 200. In another specific example, the second pump 402 may be connected on the upper portion of the depression chamber 200 and the first pump 400 may be connected to the lower portion of the depression chamber 200.

According to different examples of the invention, any other actuators can also be used in place of the first pump 400 and the second pump 402 to perform similar functions as disclosed herein.

Figure 7:
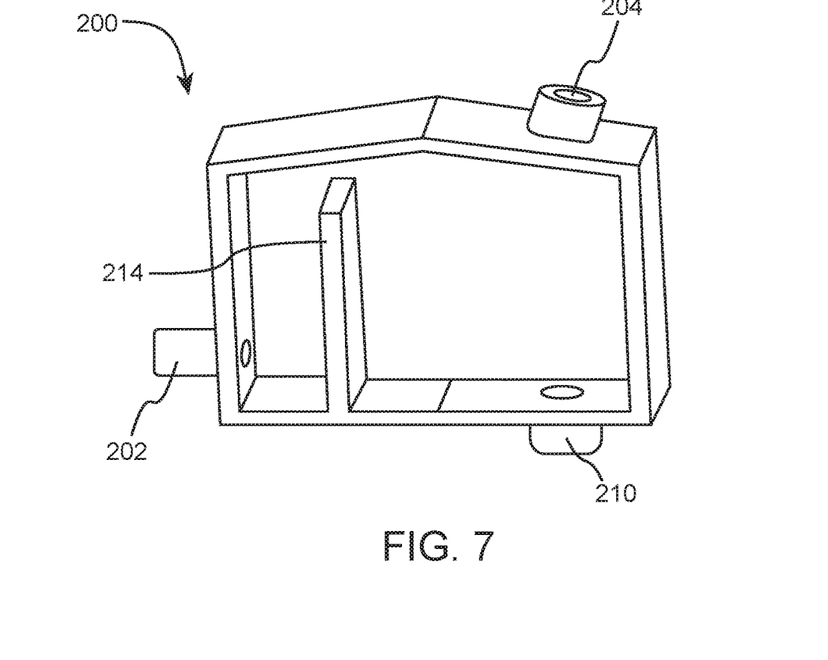
FIG. 7 illustrates an internal perspective view of the depression chamber 200 in accordance with specific embodiments of the present invention.

The depression chamber 200 can be designed/manufactured in a variety of shapes and configurations. FIG. 7 illustrates an internal perspective view of the depression chamber 200 according to an alternate embodiment of the invention. A separating wall 214 is located inside the depression chamber 200 altering the connections on the depression chamber 200. The first aperture 202 is located at a lower height than the second aperture 204. The shape of depression chamber 200 can be selected to prevent liquid from flowing out through first aperture 202 while liquid is flowing out through third aperture 210. In a particular embodiment, the vacuum pump 400 is connected to the outlet 204, the connecting line 300 is connected to the inlet 202. This connection configuration can be reversed meaning that the vacuum pump 400 is connected to the outlet 202 and the connecting line 300 is connected to the inlet 204. For both configuration, the drain pump should always be connected to the outlet with the lower altitude in order to collect the maximum of wasted fluid. When a vacuum is generated inside the depression chamber, fluids are aspirated from the connecting line 300 and fill one of the compartment of the depression chamber before being evacuated. Thus the wasted fluid aspirated never reach the vacuum pump outlet (either 202 or 204) and the vacuum pump 400 is protected.

Figure 8:
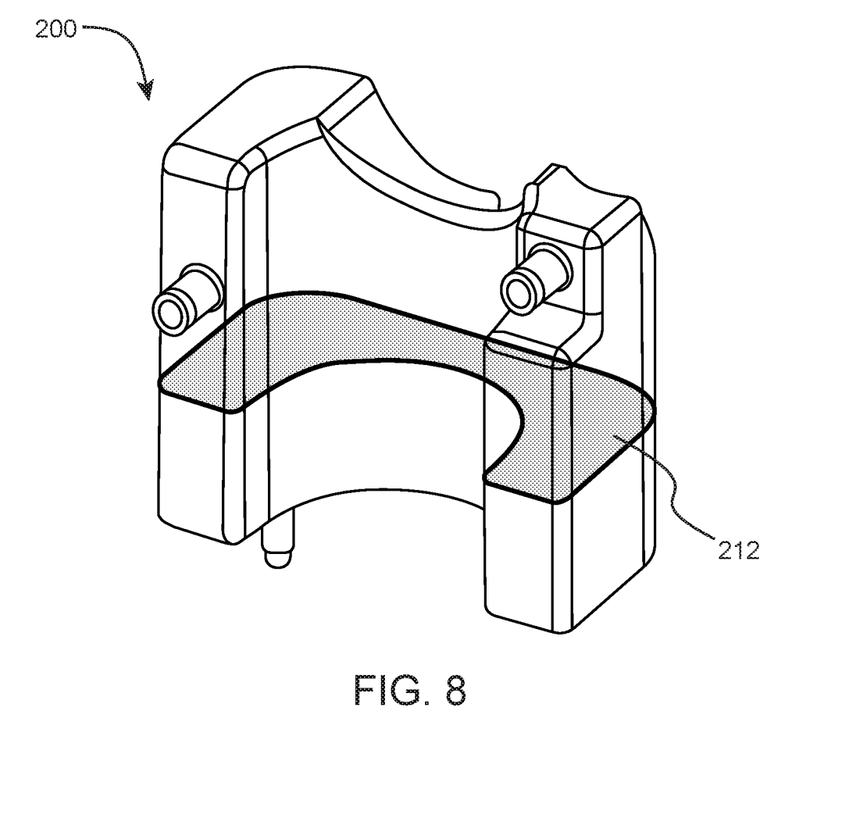
FIG. 8 illustrates a perspective view showing the placement of an anti-foam mesh/grid 212 inside the depression chamber 200 in accordance with specific embodiments of the present invention.

According to still another embodiment of the invention, an anti-foam mesh/grid 212 is placed inside the depression chamber 200. FIG. 8 illustrates a perspective view showing the placement of the anti-foam mesh/grid 212 inside the depression chamber 200. The anti-foam mesh/grid 212 may be used to protect the first pump 400 against foam and liquid flow, thereby improving the lifespan of the first pump 400 as well as the oral care appliance 1 in general. The anti-foam mesh/grid 212 used can be used from any material suitable for destroying the foam inside the chamber 200. For instance, it may be made of stainless steel or other stainless metal. In one embodiment, the anti-foam mesh can be made of finely meshed stainless steel, the small cells of such a mesh limit the space available and thus prevent the foam from expanding. In another embodiment, the anti-foam is made of a polyurethane foam that absorbs the liquid present in the mix of air and liquid in the foam and thus prevents the foam from forming.

In yet another embodiment of the invention, the anti-foam mesh/grid 212 may be placed between inlet for the first pump 400 and the second pump 402. In an alternate embodiment, the anti-foam mesh/grid 212 may be located at the bottom of the depression chamber 200 in proximity to the third aperture 210.

In yet another embodiment of the present invention, the anti-foam mesh/grid 212 can be located inside the depression chamber 200 in a way that the first pump 400 is located on its one side and the second pump 402 is located on its other side wherein the second pump 402 drains the waste out from the depression chamber 200.

In yet another embodiment of the invention, heating effects may be used inside the depression chamber 200 for preventing the foam form forming in the chamber 200.

In yet another embodiment of the invention, high frequency pulses such as ultrasounds/ultrasonic waves may be used inside the depression chamber 200 for treating/preventing the foam created in the depression chamber 200.

In yet another embodiment of the invention, filters may be placed between the mouthpiece 100 and the depression chamber 200 for treating/preventing the foam in the depression chamber 200.

In yet another embodiment of the invention, filters may be placed between the mouthpiece 100 and the depression chamber 200 for preventing the transfer of large debris that could accumulate inside the depression chamber.

In yet another embodiment of the invention, the depression chamber 200 is provided with means for limiting the fluid flow such as one or more chicane arrangements for treating/preventing the foam in the waste.

In yet another embodiment of the invention, treatment of waste can be done inside the depression chamber 200 for preventing the foam formation by the methods known to the person skilled in the art.

According to another embodiment of the invention, a brushing cycle comprises a sequence of an oral care composition injection inside the mouthpiece followed by contraction and relaxation phases. The oral care composition can be injected into the mouthpiece by creating a pressure difference between the inside of the mouthpiece and the supply tank. The pressure difference can be negative or positive. The injection cycle is followed by a contraction cycle in which the waste is drained out from the mouthpiece and the mouthpiece contracts on the dental arch followed by a relaxation cycle in which ambient air is injected into the mouthpiece taking the mouthpiece back to its original shape so that it moves away from the dental arch. Alternating sequences of one or several oral care composition injections followed by many contraction and relaxation phases can be performed to complete a brushing cycle.

Figure 9:
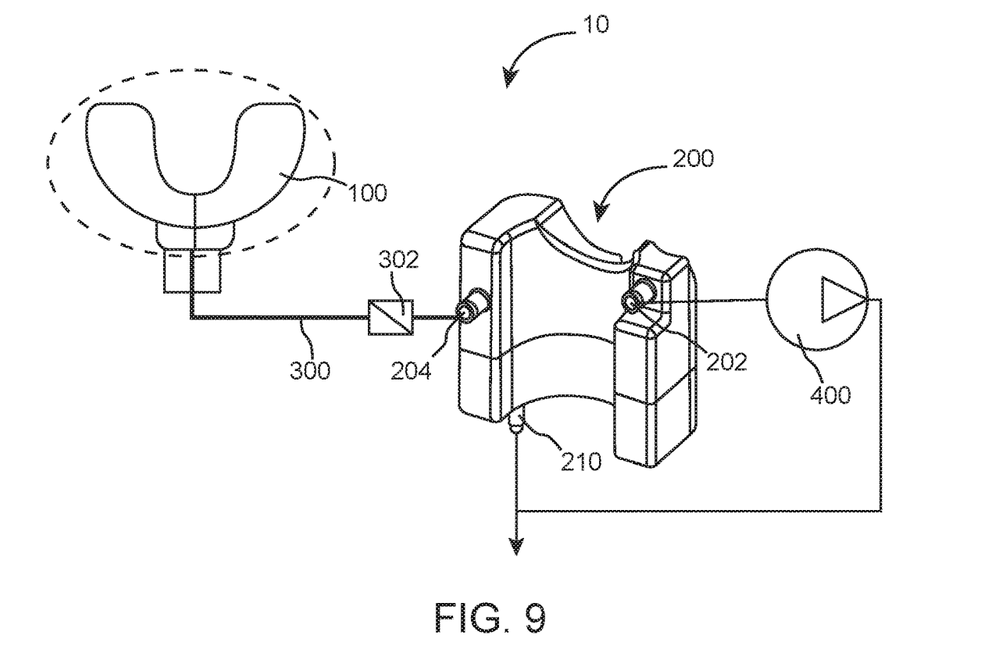
FIG. 9 illustrates a method of operation of an oral care appliance during a brushing cycle in accordance with specific embodiments of the present invention.

According to another embodiment of the invention as illustrated in FIG. 9, a method for operating an oral care appliance in a brushing cycle is described. The oral care appliance comprises a mouthpiece 100; depression chamber 200 having a plurality of apertures 202, 204, 210; a first pump 400 attached to the first aperture 202; and a connecting line 300 connecting the mouthpiece 100 with the second aperture 204 of the depression chamber 200. The connecting line 300 comprises a valve 302 to control the communication between the mouthpiece 100 and the depression chamber 200. The method for operating an oral care appliance comprises the steps of: generating vacuum in the depression chamber 200 by means of the first pump 400 attached to the first aperture 202 of the depression chamber 200; opening the first valve 302 coupled to the connecting line 300 between the mouthpiece 100 and the second aperture 204 of the depression chamber 200 to create a pressure difference between the mouthpiece 100 and the ambient atmosphere and facilitate the contraction of the mouthpiece 100 on a dental arch of a user, thereby aspirating a fluid from the mouthpiece 100 to the depression chamber 200 through the connecting line 300; closing the first valve 302 to facilitate the relaxation of the mouthpiece 100 wherein vacuum is again created in the depression chamber 200 by means of the first pump 400.

According to another embodiment of the invention, the first pump 400 is operatively engaged to generate a vacuum/depression inside the depression chamber 200; particularly inside the reservoir 206 of the depression chamber 200. The vacuum/depression created in the depression chamber 200 creates a negative pressure between the inside of the mouthpiece 100 and the ambient atmosphere when the valve 302 is in open position, thereby enabling the mouthpiece 100 to contract on the dental arch of the user and subsequently, aspirating the fluid out from the mouthpiece 100 to the depression chamber 200. The fluid can be air during the starting phase of the brushing cycle according to specific example of the invention.

According to specific embodiment of the invention, the first pump 400 is always running regardless of the position of the valve 302 to create the suitable depressions inside the depression chamber 200. The magnitude or speed with which the depressions are generated affects the efficiency of the oral care appliance 10. Thus, the continuous depressions created in the depression chamber 200 allow to reach an air depression level faster in the mouthpiece 100 which subsequently increases the efficiency of the appliance 10. In certain situations such a set of embodiments outperforms an alternative approach in which a pump creates the depression periodically in step with the required delivery of cycles of compression and relaxation in mouthpiece 100.

According to specific embodiment of the invention, the depression chamber 200 and more specifically the reservoir 206 enclosed between the walls of the depression chamber 200 acts as a vacuum reservoir allowing the drainage of the waste from the mouthpiece while maintaining the pressure difference between the inside and the outside of the depression chamber.

According to specific embodiment of the invention, the vacuum is continuously created in the depression chamber 200 to increase the speed of contractions inside the mouthpiece 100. Thus, the requirement for providing several contraction/relaxation cycles during the brushing cycle is achieved by continuously creating the vacuum inside the chamber 200. Thereby, continuous depressions inside the depression chamber allow continuous pulses of injection/contractions in an oral care appliance.

According to an exemplary embodiment of the invention, a passive solution may be used, such as a check valve, a pressure relief valve, in order to control the communication between the first pump 400 and the depression chamber 200, thus allowing to control the level of depressions inside the chamber 200.

According to a specific embodiment of the invention, as illustrated in FIG. 9, the output of the first pump 400 can be connected to a third aperture 210 of the depression chamber 200 to allow the drainage of waste/fluid out form the aperture 210.

Figure 10:
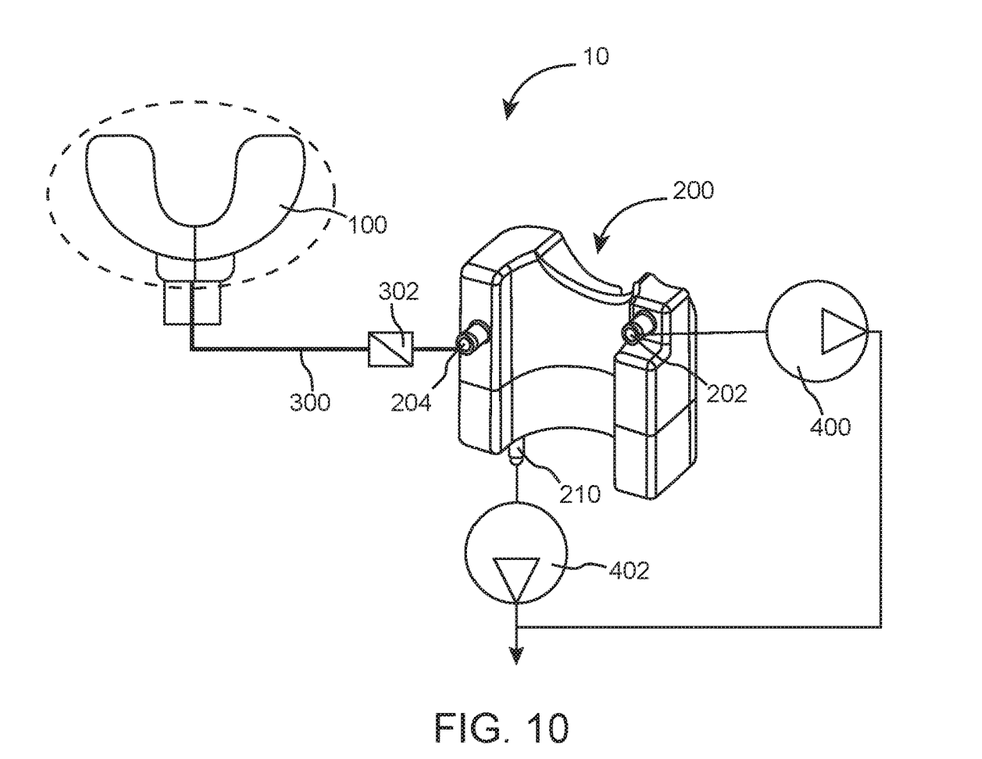
FIG. 10 illustrates the draining of the waste/fluid by the second pump 402 during a method of operation of the oral care appliance during a brushing cycle in accordance with specific embodiments of the present invention.

According to another embodiment of the invention as illustrated in FIG. 10, a method for operating an oral care appliance in a brushing cycle, wherein a pump 402 is arranged with the third aperture 210 of the depression chamber 200. The second pump 402 drains the waste from the depression chamber 200. According to specific embodiment of the invention, the second pump 402 can be a one-way pump used for draining out waste liquids. According to another specific embodiment of the invention, the second pump 402 can be a peristaltic pump or any other pump suitable for draining out the waste from the depression chamber 200. The peristaltic pump offers easy maintenance as compared to other pumping technologies. The peristaltic pump comprises flexible tubing running through rollers in the pump head. As fluid goes through the pump head, packets of fluid are formed. The only part of the peristaltic pump that encounters the fluid is tubing. This limits contacts between the fluid and mechanical parts of the pump in order to minimize its wear. Furthermore, a peristaltic pump is a one-way pump meaning that at any moment of its operating no opposite flow can go through the pump. This property enables the pump 402 to seal the depression chamber 200.

According to another embodiment of the invention, the method for operating an oral care appliance comprises the steps of: generating vacuum in the depression chamber 200 by means of the first pump 400 attached to the first aperture 202 of the depression chamber 200; opening the first valve 302 coupled to the connecting line 300 between the mouthpiece 100 and the second aperture 204 of the depression chamber 200 subsequently, the pressure inside the mouthpiece decreases relative to ambient pressure and, thus, facilitates the contraction of the mouthpiece 100 on a dental arch of the user and thereby aspirating a fluid out from the mouthpiece 100 to the depression chamber 200 through the connection line 300; after a certain amount of time, or alternatively, once the pressure difference between the inside of the cavity and ambient pressure reaches a calibrated value, closing the first valve 302 coupled to the connecting line 300; the pressure inside the mouthpiece can be measured by means of pressure sensor or other means; closing the first valve 302 to facilitate the relaxation of the mouthpiece 100 wherein vacuum is again created in the depression chamber 200 by means of the first pump 400. In this embodiment, the pump 402 connected to the third aperture 210 seals the depression chamber 200 as it does not let air flow through it and prevent the loss of vacuum created in the depression chamber 200. In this embodiment, the pump 400 can always be running to create continuous vacuum in the depression chamber 200 during the brushing cycle. Furthermore, the pump 402 can also always be running to continuously drain the depression chamber and avoid overflowing of the depression chamber.

According to exemplary embodiment of the invention, the particular time can be between 10-1000 ms and the certain pressure difference relative to ambient pressure can be between −100 kPa to 200 kPa. The time and pressure can vary depending upon the use and the requirements of the brushing cycle without departing from the spirit and the scope of the invention.

Figure 11:
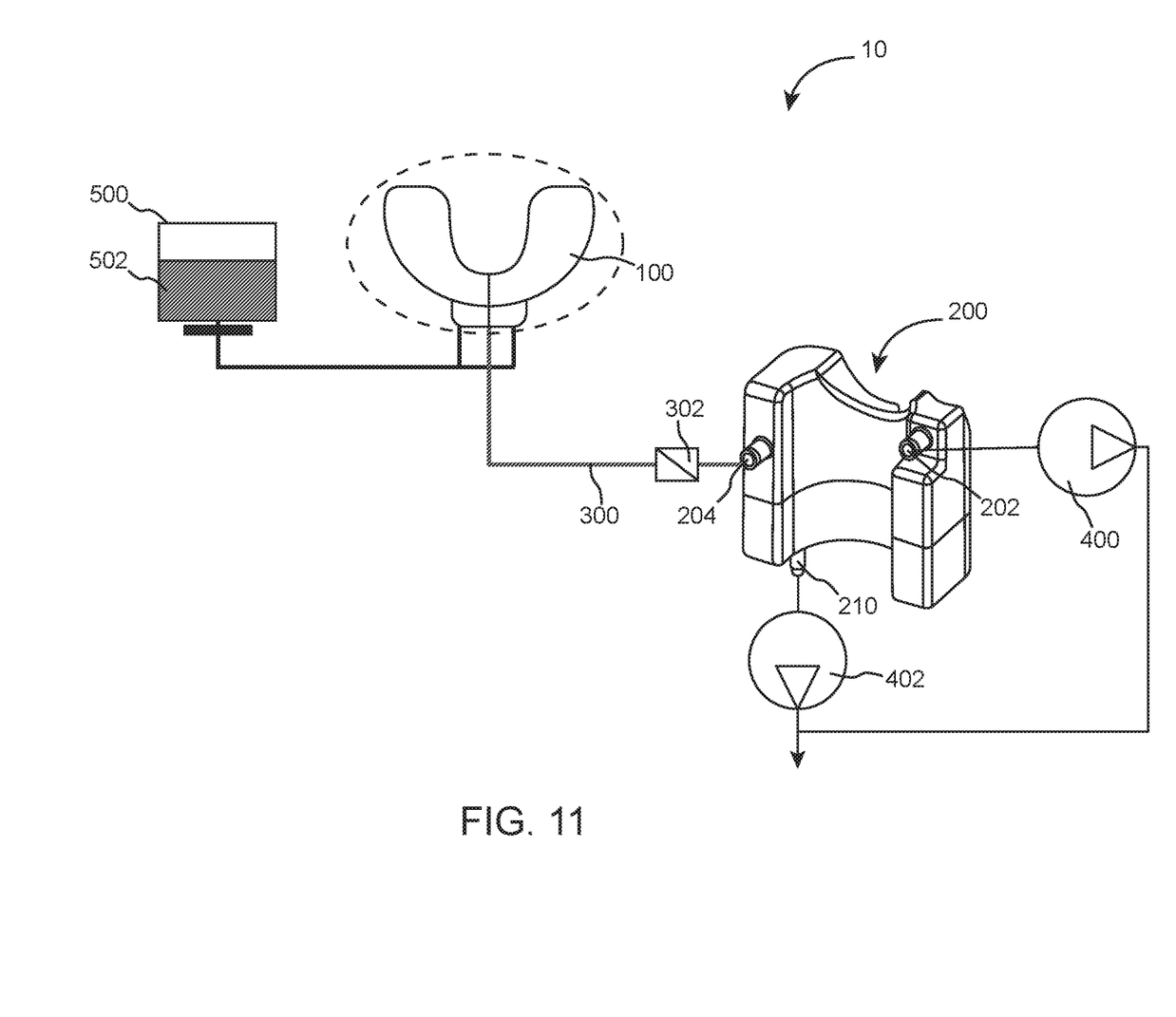
FIG. 11 illustrates the injection of an oral care composition 502 in the mouthpiece 100 during a method of operation of the oral care appliance during a brushing cycle in accordance with specific embodiments of the present invention.

According to another embodiment of the invention as illustrated in FIG. 11, a method for operating an oral care appliance in a brushing cycle, a supply tank 500 is provided with an oral care composition 502, where the supply tank is connected to the mouthpiece 100 by a connecting line between the supply tank 500 and the mouthpiece 100. The method for operating an oral care appliance comprises the steps of: generating vacuum in the depression chamber 200 by means of the first pump 400 attached to the first aperture 202 of the depression chamber 200; opening the first valve 302 coupled to the connecting line 300 between the mouthpiece 100 and the second aperture 204 of the depression chamber 200, the pressure inside the mouthpiece 100 decreases relative to ambient pressure thus enabling the contraction of the mouthpiece on a dental arch of a user. The negative pressure inside the mouthpiece 100 leads to the aspiration of the oral care composition 502 from the supply tank 500 to the mouthpiece; after a certain amount of time, or alternatively, once the pressure difference between the inside of the cavity and ambient pressure reaches a calibrated value, closing the first valve 302 to again create a depression in the depression chamber 200 with the help of the first pump 400; after a certain amount of time, or alternatively, once the pressure difference between the inside of the cavity and ambient pressure is reached, opening the first valve 302 thereby aspirating the waste out from the mouthpiece 100 to the depression chamber 200 through the connection line 300; after a certain amount of time, or alternatively, once the pressure difference between the inside of the cavity and ambient pressure reaches a calibrated value, closing the first valve 302 to facilitate the relaxation of the mouthpiece 100 wherein vacuum is again created in the depression chamber 200 by means of the first pump 400. The pressure inside the mouthpiece can be measured by means of pressure sensor or other means. The second pump 402 drains the wasted liquid from the depression chamber 200 to the sink. The second pump 402 connected to the third aperture 210 seals the depression chamber 200 as it does not let air flowing through it and prevent the loss of vacuum created in the depression chamber 200. In these embodiments, the pump 400 can always be running to create a continuous vacuum in the depression chamber 200 during the brushing cycle.

According to another embodiment of the invention, the valve 302 can be open or close for a set time defined by a timer. The set time can be chosen depending on the requirements of the brushing cycle.

Figure 12:
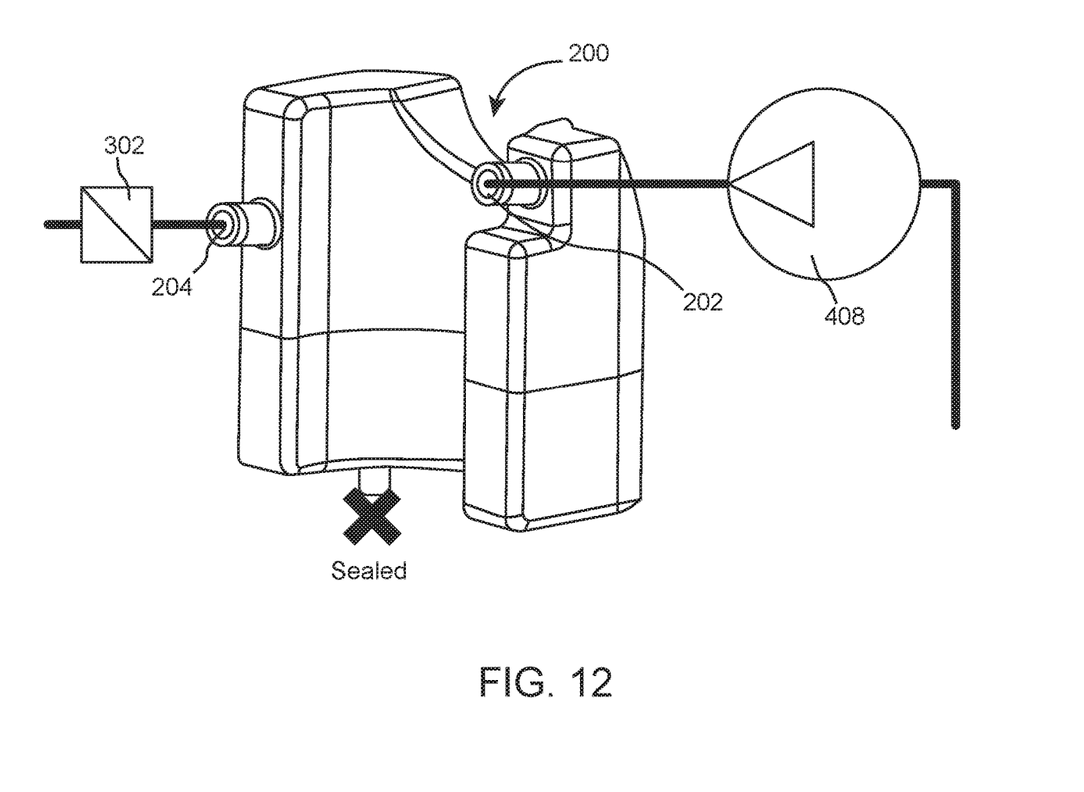
FIG. 12 illustrated an alternate embodiment of functioning of the depression chamber 200 in accordance with specific embodiments of the present invention.

According to another embodiment of the invention as illustrated in FIG. 12. The method for operating an oral care appliance comprises the steps of: generating a positive pressure in the depression chamber 200 by means of a pump 408 attached to the first aperture 202 of the depression chamber 200. The pump 408 is increasing the pressure inside the depression chamber 200 relative to ambient pressure by injecting air or liquid into the depression chamber 200; thereby opening the first valve 302 after the pressure inside the depression chamber reaches a monitored value or after a particular time period to increase the pressure inside the mouthpiece by the air or liquid flow into the mouthpiece from the depression chamber 200. According to another embodiment the depression chamber 200 can act as pressure chamber to increase the speed of the establishment of a positive pressure in the mouthpiece 100.

According to another specific embodiment of the invention, the second pump 402 can be a two-way pump having a check valve 404 in between the pump 402 and the depression chamber 200. The check valve 404 prevents the air from entering the depression chamber 200 as this phenomenon can affect the vacuum created inside the depression chamber 200. According to another specific embodiment, the position of the check valve 404 is reversed when the depression chamber 200 acts as a pressure chamber to increase the speed of the establishment of a positive pressure in the mouthpiece 100.

According to another specific embodiment of the invention, the method for operating the oral care appliance can be used on multiple dental arches simultaneously.

According to another specific embodiment of the invention, a single depression chamber can be connected to multiple mouthpieces, thereby creating pressure difference in the multiple mouthpieces.

According to another specific embodiment of the invention, a tailor-made pump can be used with the mouthpiece 100 to create the pressure difference inside the mouthpiece 100. According to a different example, the tailor-made pump, and an associated membrane and mouthpiece, can be used with the depression chamber 200 to enhance the magnitude and speed to generate depressions inside the chamber 200.

According to another specific embodiment of the invention, the waste is drained at the end of the brushing cycle. The waste can be manually drained from the depression chamber 200.

One or more of the above-mentioned embodiments/steps of the present invention can be automated completely or partially using one or more of a control system, timer, pressure sensor and software.

Although the invention has been described with regard to its embodiments, specific embodiments and various examples, it should be understood that various changes and modifications as would be obvious to one having the ordinary skill in this art may be made without departing from the scope of the invention as set forth in the claims appended hereto.

What is claimed is:

1. An oral care appliance comprising:
    a mouthpiece comprising a flexible membrane configured to deform in response to pressure variations generated in a cavity resulting in volume changes of the cavity;
    a depression chamber having a plurality of apertures and configured to generate the pressure variations in the cavity;
    a first pump: (i) engaged with a first aperture of the depression chamber; and (ii) configured to generate a vacuum in the depression chamber;
    a second aperture of the depression chamber connected to the mouthpiece through a connecting line;
    a third aperture of the depression chamber with a lower height than the first and second apertures; and
    a second pump: (i) engaged with the third aperture of the depression chamber; and (ii) configured to drain fluids from the depression chamber via the third aperture.

2. The oral care appliance according to claim 1, further comprising a valve mechanism coupled to the connecting line; and wherein the valve mechanism is adapted for communication between the depression chamber and the mouthpiece.

3. The oral care appliance according to claim 2, wherein the valve mechanism comprises an electrically or mechanically operated valve.

4. The oral care appliance according to claim 2, wherein the first pump is configured to create a pressure difference between the depression chamber and the cavity, when the valve mechanism is in an open position, leading to aspiration of air/fluid from the mouthpiece to the depression chamber.

5. The oral care appliance according to claim 1, wherein the cavity is a space between a dental arch and the flexible membrane.

6. The oral care appliance according to claim 1, wherein a gripping pressure of the mouthpiece is operable to change the deformation of the flexible membrane on a dental arch.

7. The oral care appliance according to claim 1, wherein the first pump is configured to aspirate air and fluids from the mouthpiece into the depression chamber.

8. The oral care appliance according to claim 1, wherein the second pump is a one-way pump.

9. The oral care appliance according to claim 1, wherein the first pump is connected to an upper portion of the depression chamber and the second pump is connected to a lower portion of the depression chamber.

10. The oral care appliance according to claim 1, further comprising:
    an anti-foam grid located in the depression chamber.

11. The oral care appliance according to claim 10,
    wherein the anti-foam grid is located in the depression chamber such that the first pump is located on its one side and the second pump is located on its other side.

12. The oral care appliance according to claim 10, wherein the anti-foam grid is positioned at the bottom of the depression chamber in proximity to the third aperture.

13. The oral care appliance according to claim 1, wherein a valve is incorporated in relation to an inlet line or an outlet line of the second pump to prevent air flow into the depression chamber through the third aperture.

14. The oral care appliance according to claim 13, wherein the depression chamber is shaped to prevent foam and fluid from flowing through the first pump while the second pump drains the fluid out of the depression chamber.

15. A method of operating an oral care appliance in a brushing cycle comprising the steps of:
generating a vacuum in a depression chamber with a first pump attached to a first aperture of the depression chamber;
opening a first valve coupled to a connecting line between a mouthpiece and a second aperture of the depression chamber to create a pressure difference in the mouthpiece to facilitate a contraction of the mouthpiece and thereby aspirate a fluid out from the mouthpiece to the depression chamber through the connecting line;
draining fluid from the depression chamber using a second pump attached to a third aperture of the depression chamber, wherein the third aperture has a lower height than the first and second apertures; and
closing the first valve to facilitate a relaxation of the mouthpiece wherein vacuum is again created in the depression chamber using the first pump.

16. The method according to claim 15, wherein the second pump is a one-way pump.

17. The method according to claim 15, wherein the first valve is electrically or mechanically operated.

18. The method according to claim 15, wherein all of the steps are repeated a plurality of times as a plurality of brushing cycles are performed in the operation of the oral care appliance.

19. The method according to claim 15, further comprising: injecting an oral care composition into the mouthpiece through a supply tank after the pressure difference is created in the mouthpiece.

20. The method according to claim 19 further comprising: closing the first valve when the oral care composition is injected into the mouthpiece.

21. An oral care appliance comprising:
a mouthpiece comprising a flexible membrane configured to deform in response to pressure variations generated in a cavity resulting in volume changes of the cavity;
a depression chamber having a plurality of apertures and configured to generate the pressure variations in the cavity;
a first pump: (i) engaged with a first aperture of the depression chamber; and (ii) configured to generate a vacuum in the depression chamber;
a second aperture of the depression chamber connected to the mouthpiece through a connecting line; and
wherein the vacuum is continuously maintained by the first pump during the volume changes of the cavity.

22. The oral care appliance according to claim 21, further comprising a valve mechanism coupled to the connecting line; and wherein the valve mechanism is adapted for communication between the depression chamber and the mouthpiece.

23. The oral care appliance according to claim 22, wherein the first pump is configured to create a pressure difference between the depression chamber and the cavity, when the valve mechanism is in an open position, leading to aspiration of air/fluid from the mouthpiece to the depression chamber.

24. The oral care appliance according to claim 22, further comprising:
a third aperture of the depression chamber;
a second pump connected to the third aperture; and
wherein the second pump is configured to drain fluids from the depression chamber via the third aperture.

25. The oral care appliance according to claim 22, further comprising:
an anti-foam grid located in the depression chamber;
a second pump configured to drain fluids from the depression chamber; and
wherein the anti-foam grid is located in the depression chamber such that the first pump is located on its one side and the second pump is located on its other side.

26. The oral care appliance according to claim 21, wherein the cavity is a space between a dental arch and the flexible membrane.

27. The oral care appliance according to claim 21, wherein a gripping pressure of the mouthpiece is operable to change the deformation of the flexible membrane on a dental arch.

28. The oral care appliance according to claim 21, wherein the first pump is configured to aspirate air and fluids from the mouthpiece into the depression chamber.

29. A method of operating an oral care appliance in a brushing cycle comprising the steps of:
generating a vacuum in a depression chamber with a first pump attached to a first aperture of the depression chamber;
opening a first valve coupled to a connecting line between a mouthpiece and a second aperture of the depression chamber to create a pressure difference in the mouthpiece to facilitate a contraction of the mouthpiece and thereby aspirate a fluid out from the mouthpiece to the depression chamber through the connecting line;
closing the first valve to facilitate a relaxation of the mouthpiece wherein vacuum is again created in the depression chamber using the first pump; and
wherein the vacuum is thereby continuously maintained by the first pump throughout the brushing cycle.

30. The method according to claim 29, further comprising draining fluid from the depression chamber using a second pump attached at a third aperture of the depression chamber.

31. The method according to claim 30, wherein the second pump is a one-way pump.

32. The method according to claim 29, wherein the first valve is electrically or mechanically operated.

33. The method according to claim 29, wherein all of the steps are repeated a plurality of times as a plurality of brushing cycles are performed in the operation of the oral care appliance.

34. The method according to claim 29, further comprising: injecting an oral care composition into the mouthpiece through a supply tank after the pressure difference is created in the mouthpiece.

35. The method according to claim 34 further comprising: closing the first valve when the oral care composition is injected into the mouthpiece.

* * * * *